(12) United States Patent
Elbe et al.

(10) Patent No.: US 7,538,073 B2
(45) Date of Patent: *May 26, 2009

(54) PYRAZOYLCARBOXANILIDES AS FUNGICIDES

(75) Inventors: Hans-Ludwig Elbe, Wuppertal (DE); Heiko Rieck, Lyons (FR); Ralf Dunkel, Monheim (DE); Qin Zhu-Ohlbach, Düsseldorf (DE); Astrid Mauler-Machnik, Leichlingen (DE); Ulrike Wachendorff-Neumann, Neuwied (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 727 days.

This patent is subject to a terminal disclaimer.

(21) Appl. No.: 10/484,108

(22) PCT Filed: Jul. 12, 2002

(86) PCT No.: PCT/EP02/07779

§ 371 (c)(1),
(2), (4) Date: May 10, 2004

(87) PCT Pub. No.: WO03/010149

PCT Pub. Date: Feb. 6, 2003

(65) Prior Publication Data

US 2004/0204470 A1 Oct. 14, 2004

(30) Foreign Application Priority Data

Jul. 25, 2001 (DE) ................. 101 36 065

(51) Int. Cl.
*A01N 43/56* (2006.01)
(52) U.S. Cl. .................. 504/280; 548/374.1
(58) Field of Classification Search .............. 548/374.1; 504/280

See application file for complete search history.

(56) References Cited

U.S. PATENT DOCUMENTS

| | | | |
|---|---|---|---|
| 3,917,592 A | 11/1975 | Kobzina | 260/244 |
| 4,032,573 A | 6/1977 | Kaneko et al. | 260/562 N |
| 4,194,008 A | 3/1980 | Enders et al. | 424/322 |
| 5,223,526 A | 6/1993 | McLoughlin et al. | 514/406 |
| 5,438,070 A | 8/1995 | Eicken et al. | 514/403 |
| 5,480,897 A * | 1/1996 | Eicken et al. | 514/365 |
| 5,914,344 A | 6/1999 | Yoshikawa et al. | 514/406 |
| 5,965,774 A | 10/1999 | Yoshikawa et al. | 564/305 |
| 6,147,104 A | 11/2000 | Eicken et al. | 514/406 |
| 6,369,093 B1 | 4/2002 | Elbe et al. | 514/406 |
| 2006/0089399 A1* | 4/2006 | Dunkel et al. | 514/406 |

FOREIGN PATENT DOCUMENTS

| | | |
|---|---|---|
| EP | 0 545 099 | 6/1993 |
| JP | 63048269 A * | 2/1988 |
| WO | 02/08195 | 1/2002 |

OTHER PUBLICATIONS

Heterocycles, vol. 29, No. 6, (month unavailable) 1989, pp. 1013-1016, Yoshinori Kondo et al, "Palladium-Catalyzed Indole and Benzofuran Ring Formation Accompanying Carbonylation".

J. Med. Chem. 39(4), (month unavailable) 1996, pp. 892-903, Lee F. Kuyper et al, "High-Affinity Inhibitors of Dihydrofolate Reductase: Antimicrobial and Anticaner Activities of 7,8-Dialkyl-1,3-diaminopyrrolo[3,2f]quinazolines with Small Molecular Size".

Synthesis, (6), Jun. 1995, pp. 713-716, Michael Harmata et al, "A General, Regioselective Synthesis of 2-Alkenylanilines".

Synth. Commun. 24(2) (month unavailable) 1994, pp. 267-272, Maryam Hojjat et al, "An Activated Trifluoromethyl Group as a Novel Synthon for a Substituted Vinyl Function: Facile Synthesis of 2-(Substituted 1-Alkenyl)Anilines".

Synthesis (2), Feb. 1994, pp. 142-144, Michael Harmata et al, "A General, Regioselective Synthesis of 2-Alkylaniles".

J. Am. Chem. Soc., 100(15), Jul. 19, 1978, pp. 4842-4852, Tsutomu Sugasawa et al, "Aminohaloborane in Organic Synthesis. 1. Specific Ortho Substitution Reaction of Anilines".

Justus Liebigs Ann. Chem. (580), (month unavailable) 1953, pp. 44-57, Von Georg Wittig und George Geissler, "Zur Reaktionsweise des Pentaphenyl-phosphors und einiger Derivate".

Pure Appl. Chem. (9), (month unavailable) 1964, pp. 307-335, B.A. Arbusow, "Michaelis-Arbusow- Und Perkow-Reaktionen".

(Continued)

*Primary Examiner*—Rebecca L Anderson
*Assistant Examiner*—Jason Nolan
(74) *Attorney, Agent, or Firm*—Richard E. L. Henderson

(57) ABSTRACT

The present invention relates to novel pyrazolylcarboxanilides of the formula (I)

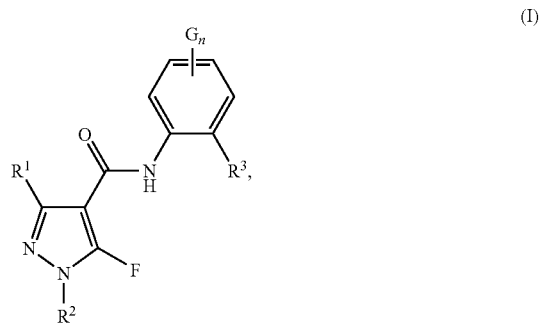

in which $R^1$, $R^2$, G, $R^3$ and n are as defined in the disclosure, to a plurality of processes for preparing these substances and their use for controlling undesirable microorganisms and to novel intermediates and their preparation.

16 Claims, No Drawings

OTHER PUBLICATIONS

Database CA 'Online Chemical Abstracts Service, Columbus, Ohio, US; Nishida, Sumio et al: "Preparation of 5-fluoro-pyrazole-4-carboxamides as agrochemical microbicides" retrieved from STN Database accession No. 109:231009 XP002218232 in der Anmeldung erwähnt Zusammenfassung & JP 63 048269 A (Sumitomo Chemical Co., Ltd., Japan) Feb. 29, 1988.

Database CA 'Online! Chemical Abstracts Service, Columbus, Ohio, US; Nishida, Sumio et al: "Preparation of 3'-isopropoxy-2'-methylanilides as fungicides" retrieved from STN Database accession No. 109:124408 XP002218233 Zusammenfassung & JP 62 249975 A (Sumitomo Chemical Co., Ltd., Japan) Oct. 30, 1987.

* cited by examiner

PYRAZOYLCARBOXANILIDES AS FUNGICIDES

The present patent application has been filed under 35 U.S.C. 371 as a national stage application of PCT/EP02/07779, filed Jul 12, 2002, which was published in German as International Patent Publication WO 03/010149 on Feb. 6, 2003, which is entitled to the right of priority of German Patent Application 101 36 065.7, filed Jul 25, 2001.

The present invention relates to novel pyrazolylcarboxanilides, to a plurality of processes for their preparation and to their use for controlling undesirable microorganisms.

It is already known that numerous carboxanilides have fuingicidal properties (compare WO 93-11117, EP-A 0 545 099, EP-A 0 589 301, WO 99/09013, DE 198 40 322, EP-A 0 824 099, JP 63048269). Thus, N-(2-cyclohexyl)-1,3-dimethyl-5-fluoropyrazol-4-carboxanilide, N-(2-phenyl)-1,3-dimethylpyrazol-4-carboxanilide and N-[2-(2-fluorophenyl)]-1,3-dimethylpyrazol-4-carboxanilide can be used for controlling fungi. The activity of these substances is good; however, at low application rates it is sometimes unsatisfactory.

This invention now provides novel pyrazolylcarboxanilides of the formula (I)

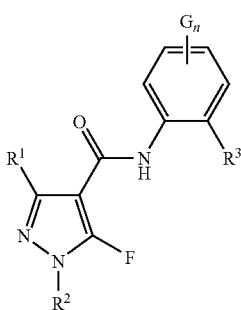

(I)

in which
R$^1$ represents hydrogen, cyano, halogen, nitro, $C_1$-$C_4$-alkyl, $C_1$-$C_4$-haloalkyl having 1 to 5 halogen atoms, $C_3$-$C_6$-cycloalkyl, $C_1$-$C_4$-alkoxy, $C_1$-$C_4$-haloalkoxy having 1 to 5 halogen atoms, $C_1$-$C_4$-alkylthio, $C_1$-$C_4$-haloalkylthio having 1 to 5 halogen atoms or aminocarbonyl-$C_1$-$C_4$-alkyl,
R$^2$ represents hydrogen, $C_1$-$C_4$-alkyl, $C_1$-$C_6$-haloalkyl having 1 to 5 halogen atoms, $C_2$-$C_6$-alkenyl, $C_3$-$C_6$-cycloalkyl, $C_1$-$C_4$-alkylthio-$C_1$-$C_4$-alkyl, $C_1$-$C_4$-haloalkylthio-$C_1$-$C_4$-alkyl having 1 to 5 halogen atoms, $C_1$-$C_4$-alkoxy-$C_1$-$C_4$-alkyl or $C_1$-$C_4$-haloalkoxy-$C_1$-$C_4$-alkyl having 1 to 5 halogen atoms,
G represents halogen or $C_1$-$C_4$-alkyl,
G furthermore represents $C_5$-$C_6$-alkyl,
R$^3$ represents unsubstituted $C_2$-$C_{20}$-alkyl or represents $C_1$-$C_{20}$-alkyl which is mono- or polysubstituted by identical or different substituents from the group consisting of halogen and/or $C_3$-$C_6$-cycloalkyl or represents $C_2$-$C_{20}$-alkenyl or $C_2$-$C_{20}$-alkynyl, each of which is optionally mono- or polysubstituted by identical or different substituents from the group consisting of halogen and/or $C_3$-$C_6$-cycloalkyl, where the cycloalkyl moiety for its part may optionally be mono- or polysubstituted by identical or different substituents from the group consisting of halogen and/or $C_1$-$C_4$-alkyl and
n represents 0, 1 or 2.

If appropriate, the compounds according to the invention can be present as mixtures of different possible isomeric forms, in particular of stereoisomers, such as, for example, E and Z, threo and erythro, and also optical isomers, and, if appropriate, also as tautomers. What is claimed are both the E and the Z isomers, and the threo and erythro and also the optical isomers, any mixtures of these isomers, and also the possible tautomeric forms.

Furthermore, it has been found that pyrazolylcarboxanilides of the formula (I) are obtained when
a) carboxylic acid derivatives of the formula (II)

(II)

in which
R$^1$ and R$^2$ are as defined above and
X represents halogen,
are reacted with an aniline derivative of the formula (III)

(III)

in which
G, R$^3$ and n are as defined above,
if appropriate in the presence of an acid binder and if appropriate in the presence of a diluent, or
b) pyrazolylcarboxanilides of the formula (Ia)

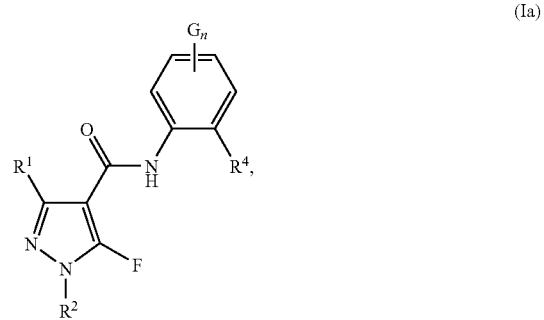

(Ia)

in which
R$^1$, R$^2$, G and n are as defined above and
R$^4$ represents $C_2$-$C_{20}$-alkenyl or $C_2$-$C_{20}$-alkynyl, each of which is optionally mono- or polysubstituted by identical or different substituents from the group consisting of halogen and/or $C_3$-$C_6$-cycloalkyl, where the cycloalkyl moiety for its part may optionally be substituted by halogen and/or $C_1$-$C_4$-alkyl,
are hydrogenated, if appropriate in the presence of a diluent and if appropriate in the presence of a catalyst, or c) hydroxyalkylpyrazolylcarboxanilides of the formula (IV)

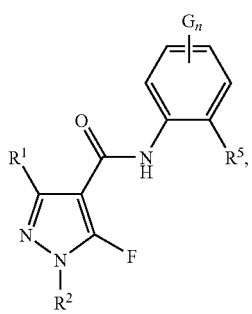

(IV)

in which
R¹, R², G and n are as defined above and
R⁵ represents $C_2$-$C_{20}$-hydroxyalkyl which is optionally additionally mono- or polysubstituted by identical or different substituents from the group consisting of halogen and/or $C_3$-$C_6$-cycloalkyl, where the cycloalkyl moiety for its part may optionally be substituted by halogen and/or $C_1$-$C_4$-alkyl,
is dehydrated, if appropriate in the presence of a diluent and if appropriate in the presence of an acid, or d) halopyrazolylcarboxanilides of the formula (V)

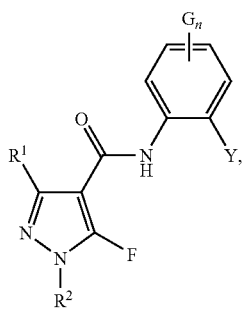

(V)

in which
R¹, R², G and n are as defined above and
Y represents bromine or iodine,
are reacted with an alkyne of the formula (VI)

  (VI), in which
R⁶ represents $C_2$-$C_{18}$-alkyl which is optionally mono- or polysubstituted by identical or different substituents from the group consisting of halogen and/or $C_3$-$C_6$-cycloalkyl, where the cycloalkyl moiety for its part may optionally be substituted by halogen and/or $C_1$-$C_4$-alkyl,
or an alkene of the formula (VII)

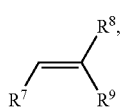

(VII)

in which
R⁷, R⁸ and R⁹ independently of one another each represent hydrogen or alkyl which is optionally mono- or polysubstituted by identical or different substituents from the group consisting of halogen and/or $C_3$-$C_6$-cycloalkyl, where the cycloalkyl moiety for its part may optionally be substituted by halogen and/or $C_1$-$C_4$-alkyl and where the total number of carbon atoms of the open-chain moiety does not exceed the number 20,
if appropriate in the presence of a diluent, if appropriate in the presence of an acid binder and in the presence of one or more catalysts, or e) ketones of the formula (VIII)

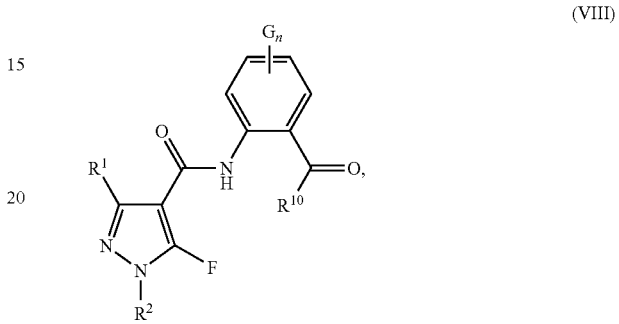

(VIII)

in which
R¹, R², G and n are as defined above and
R¹⁰ represents hydrogen or $C_1$-$C_{18}$-alkyl which is optionally mono- or polysubstituted by identical or different substituents from the group consisting of halogen and/or $C_3$-$C_6$-cycloalkyl, where the cycloalkyl moiety for its part may optionally be substituted by halogen and/or $C_1$-$C_4$-alkyl,
are reacted with a phosphorus compound of the general formula (IX)

$R^{11}$—Px  (IX), in which
R¹¹ represents hydrogen or $C_1$-$C_{18}$-alkyl which is optionally mono- or polysubstituted by identical or different substituents from the group consisting of halogen and/or $C_3$-$C_6$-cycloalkyl, where the cycloalkyl moiety for its part may optionally be substituted by halogen and/or $C_1$-$C_4$-alkyl and
Px represents a grouping —P⁺($C_6H_5$)₃ Cl⁻, —P⁺($C_6H_5$)₃ Br⁻, —P⁺($C_6H_5$)₃ I⁻, —P(=O)(OCH₃)₃ or —P(=O)(OC₂H₅)₃,
if appropriate in the presence of a diluent.

Finally, it has been found that the novel pyrazolylcarboxanilides of the formula (I) have very good microbicidal properties and can be used for controlling undesirable microorganisms both in crop protection and in the protection of materials.

Surprisingly, the pyrazolylcarboxanilides of the formula (I) according to the invention have considerably better fungicidal activity than the constitutionally most similar active compounds of the prior art having the same direction of action.

The formula (I) provides a general definition of the pyrazolylcarboxanilides according to the invention.

R¹ preferably represents hydrogen, cyano, halogen, nitro, $C_1$-$C_4$-alkyl, $C_1$-$C_4$-haloalkyl having 1 to 5 fluorine, chlorine and/or bromine atoms, $C_3$-$C_6$-cycloalkyl, $C_1$-$C_4$-alkoxy, $C_1$-$C_4$-haloalkoxy having 1 to 5 fluorine, chlorine and/or bromine atoms, $C_1$-$C_4$-alkylthio, $C_1$-$C_4$-haloalkylthio having 1 to 5 fluorine, chlorine and/or bromine atoms or aminocarbonyl-$C_1$-$C_4$-alkyl.

$R^2$ preferably represents hydrogen, $C_1$-$C_4$-alkyl, $C_1$-$C_6$-haloalkyl having 1 to 5 fluorine, chlorine and/or bromine atoms, $C_2$-$C_6$-alkenyl, $C_3$-$C_6$ cycloalkyl, $C_1$-$C_4$-alkylthio-$C_1$-$C_4$-alkyl, $C_1$-$C_4$-haloalkylthio-$C_1$-$C_4$-alkyl having 1 to 5 fluorine, chlorine and/or bromine atoms, $C_1$-$C_4$-alkoxy-$C_1$-$C_4$-alkyl or $C_1$-$C_4$-haloalkoxy-$C_1$-$C_4$-alkyl having 1 to 5 fluorine, chlorine and/or bromine atoms.

G preferably represents halogen or $C_1$-$C_4$-alkyl.

G furthermore preferably represents $C_5$-$C_6$-alkyl.

$R^3$ preferably represents unsubstituted $C_2$-$C_{12}$-alkyl or represents $C_1$-$C_{12}$-alkyl which is mono- to tetrasubstituted by identical or different substituents from the group consisting of fluorine, chlorine, bromine and/or $C_3$-$C_6$-cycloalkyl or represents $C_2$-$C_{12}$-alkenyl or $C_2$-$C_{12}$-alkynyl, each of which is optionally mono- to tetrasubstituted by identical or different substituents from the group consisting of fluorine, chlorine, bromine and/or $C_3$-$C_6$-cycloalkyl, where the cycloalkyl moiety for its part may optionally be mono- to tetrasubstituted by identical or different substituents from the group consisting of halogen and/or $C_1$-$C_4$-alkyl.

n preferably represents 0, 1 or 2.

$R^1$ particularly preferably represents hydrogen, methyl, ethyl, n- or i-propyl, n-, i-, s- or t-butyl, trifluoromethyl or trifluoroethyl.

$R^2$ particularly preferably represents hydrogen, methyl, ethyl, n- or i-propyl, n-, i-, s- or t-butyl, trifluoromethyl or trifluoroethyl.

G particularly preferably represents fluorine, chlorine or methyl.

G furthermore particularly preferably represents ethyl or t-butyl.

G furthermore particularly preferably represents 2,4-dimethylbutyl.

$R^3$ particularly preferably represents in each case straight-chain or branched ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl or decynyl, each of which may be attached at any position and each of which is optionally mono- to tetrasubstituted by identical or different substituents from the group consisting of fluorine, cyclopropyl, difluorocyclopropyl, cyclobutyl, cyclopentyl and/or cyclohexyl.

n also particularly preferably represents 0, 1 or 2.

A very particularly preferred group are the compounds of the formula (I), in which $R^1$ represents methyl and $R^2$ represents methyl.

Very particularly preferred are furthermore compounds of the formula (I), in which $R^3$ represents unsubstituted $C_2$-$C_{20}$-alkyl (preferably $C_2$-$C_{12}$-alkyl, particularly preferably $C_2$-$C_6$-alkyl).

Very particularly preferred are furthermore compounds of the formula (I), in which n represents 0.

Emphasis is given to compounds of the formula (I), in which $R^1$ represents methyl, $R^2$ represents methyl, $R^3$ represents unsubstituted $C_2$-$C_{20}$-alkyl (preferably $C_2$-$C_{12}$-alkyl, very particularly preferably $C_2$-$C_6$-alkyl), n represents 0.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different. A plurality of radicals having the same indices, such as, for example, n radicals G for n>1, can be identical or different.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the abovementioned general or preferred radical definitions or illustrations can also be combined with one another, i.e. between the respective ranges and preferred ranges, as desired. The definitions or illustrations apply both to the end products and, correspondingly, to the precursors and intermediates.

The definitions mentioned can be combined with one another as desired. Moreover, individual definitions may not apply.

Using 5-fluoro-1,3-dimethyl-1H-pyrazol-4-carbonyl chloride and 2-(1-methylhexyl)aniline as starting materials, the process a) according to the invention can be illustrated by the following formula scheme:

The formula (II) provides a general definition of the carboxylic acid derivatives required as starting materials for carrying out the process a) according to the invention. In this formula (II), $R^1$ and $R^2$ preferably and particularly preferably have those meanings which have already been mentioned in connection with the description of the compounds of the formula (I) according to the invention as being preferred and particularly preferred for $R^1$ and $R^2$. X represents halogen, preferably chlorine.

The carboxylic acid derivatives of the formula (II) are known and/or can be prepared by known processes (cf. WO 93/11117, EP-A 0 545 099, EP-A 0 589 301 and EP-A 0 589 313).

The formula (III) provides a general definition of the anilines furthermore required for the starting materials for carrying out the process a) according to the invention. In this formula (III), G, $R^3$ and n preferably and particularly preferably have those meanings which have already been mentioned in connection with the description of the compounds of the formula (I) according to the invention as being preferred and particularly preferred for G, $R^3$ and n.

The aniline derivatives of the formula (III) are known and/or can be prepared by known methods (compare, for example, Heterocycles (1989), 29(6), 1013-16; J. Med. Chem. (1996), 39(4), 892-903; Synthesis (1995), (6), 713-16; Synth. Commun. (1994), 24(2), 267-72; DE 2727416; Synthesis (1994), (2), 142-4; EP 0 824 099).

Using 5-fluoro-1,3-dimethyl-N-{2-[(1Z)-1-methyl-1-hexenyl]phenyl}-1H-pyrazol-4-carboxamide and hydrogen as starting materials, and a catalyst, the course of the process b) according to the invention can be illustrated by the following formula scheme:

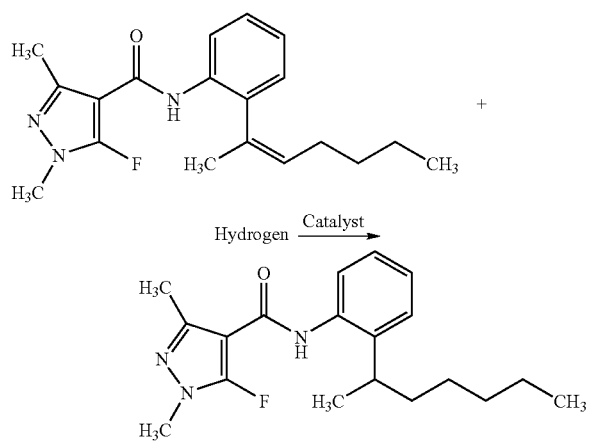

The formula (Ia) provides a general definition of the pyrazolylcarboxanilides required as starting materials for carrying out the process b) according to the invention. In this formula (Ia), $R^1$, $R^2$, G and n preferably and particularly preferably have those meanings which have already been mentioned in connection with the description of the compounds of the formula (I) according to the invention as being preferred and particularly preferred for $R^1$, $R^2$, G and n.

$R^4$ preferably represents $C_2$-$C_{12}$-alkenyl or $C_2$-$C_{12}$-alkynyl, each of which is optionally mono- to tetrasubstituted by identical or different substitutents from the group consisting of fluorine, chlorine and/or $C_3$-$C_6$-cycloalkyl, where the cycloalkyl moiety for its part may optionally be mono- to tetrasubstituted by identical or different substituents from the group consisting of halogen and/or $C_1$-$C_4$-alkyl.

$R^4$ particularly preferably represents in each case straight-chain or branched ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl or decynyl, each of which may be attached in any position and each of which is optionally mono- to tetrasubstituted by identical or different substituents from the group consisting of fluorine, cyclopropyl, difluorocyclopropyl, cyclobutyl, cyclopentyl and cyclohexyl.

The compounds of the formula (Ia) are compounds according to the invention and can be prepared by process a), c), d) or e).

Using 5-fluoro-N-[2-(1-hydroxy-1-methylhexyl)phenyl]-1,3-dimethyl-1H-pyrazol-4-carboxamide as starting material and an acid, the course of the process c) according to the invention can be illustrated by the following formula scheme:

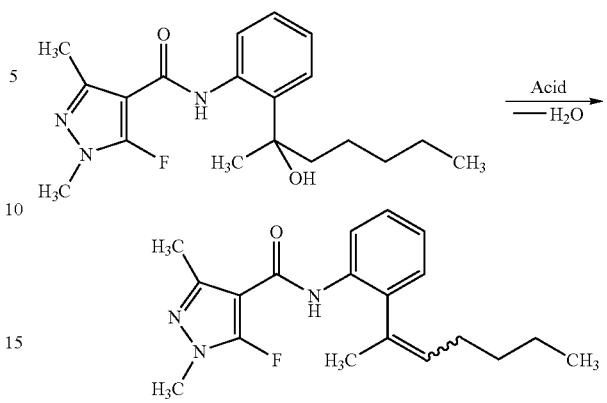

The formula (IV) provides a general definition of the hydroxyalkylpyrazolyl-carboxanilides required as starting materials for carrying out the process c) according to the invention. In this formula (V), $R^1$, $R^2$, G and n preferably and particularly preferably have those meanings which have already been mentioned in connection with the description of the compounds of formula (I) according to the invention as being preferred and particularly preferred for $R^1$, $R^2$, G and n.

$R^5$ preferably represents $C_2$-$C_{12}$-hydroxyalkyl which is optionally additionally mono- to tetrasubstituted by identical or different substituents from the group consisting of chlorine, fluorine, bromine and/or $C_3$-$C_6$-cycloalkyl, where the cycloalkyl moiety for its part may optionally be substituted by halogen and/or $C_1$-$C_4$-alkyl.

$R^5$ particularly preferably represents in each case straight-chain or branched hydroxyethyl, hydroxypropyl, hydroxybutyl, hydroxypentyl, hydroxyhexyl, hydroxyheptyl, hydroxyoctyl, hydroxynonyl or hydroxydecyl, each of which may be attached in any position and each of which is optionally mono- to tetrasubstituted by identical or different substituents from the group consisting of fluorine, cyclopropyl, difluorocyclopropyl, cyclobutyl, cyclopentyl and/or cyclohexyl.

The compounds of the formula (IV) have hitherto not been known; as novel compounds, they also form part of the subject-matter of the present application.

It has also been found that the hydroxyalkylpyrazolylcarboxanilides of the formula (IV) have very good microbicidal properties and can be used for controlling undesirable microorganisms both in crop protection and in the protection of materials.

The hydroxyalkylpyrazolylcarboxanilides of the formula (IV) are obtained when f) carboxylic acid derivatives of the formula (II)

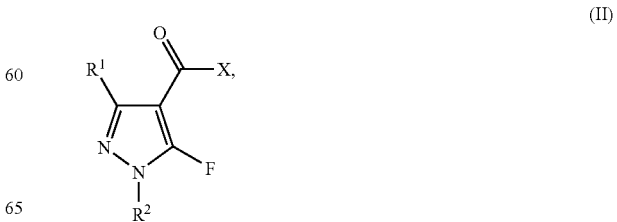

(II)

in which

R¹, R² and X are as defined above, are reacted with a hydroxyalkylaniline derivative of the formula (X)

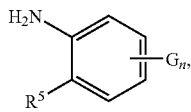

in which

R³, R⁵, G and n are as defined above, if appropriate in the presence of an acid binder and if appropriate in the presence of a diluent.

Using 5-fluoro-1,3-dimethyl-1H-pyrazol-4-carbonyl chloride and 2-(2-aminophenyl)-2-heptanol as starting materials, the course of the process f) according to the invention can be illustrated by the following formula scheme:

The carboxylic acid derivatives of the formula (II) required as starting materials for carrying out the process f) according to the invention have already been described further above, in connection with the description of the process a) according to the invention.

The formula (X) provides a general definition of the hydroxyalkylaniline derivatives furthermore required as starting materials for carrying out the process f) according to the invention. In this formula (X), R³, R⁵, G and n preferably and particularly preferably have those meanings which have already been mentioned in connection with the description of the compounds of the formulae (I) and (IV) according to the invention as being preferred and particularly preferred for R³, R⁵, G and n.

The hydroxyalkylaniline derivatives of the formula (X) are known and/or can be obtained by known methods (cf., for example, U.S. Pat. No. 3,917,592 or EP 0 824 099).

Using 5-fluoro-N-(2-iodophenyl)-1,3-dimethyl-1H-pyrazol-4-carboxamidee and 1-pentyne or alternatively 1-hexene as starting materials and in each case a catalyst and a base, the course of the process d) according to the invention can be illustrated by the two formula schemes below:

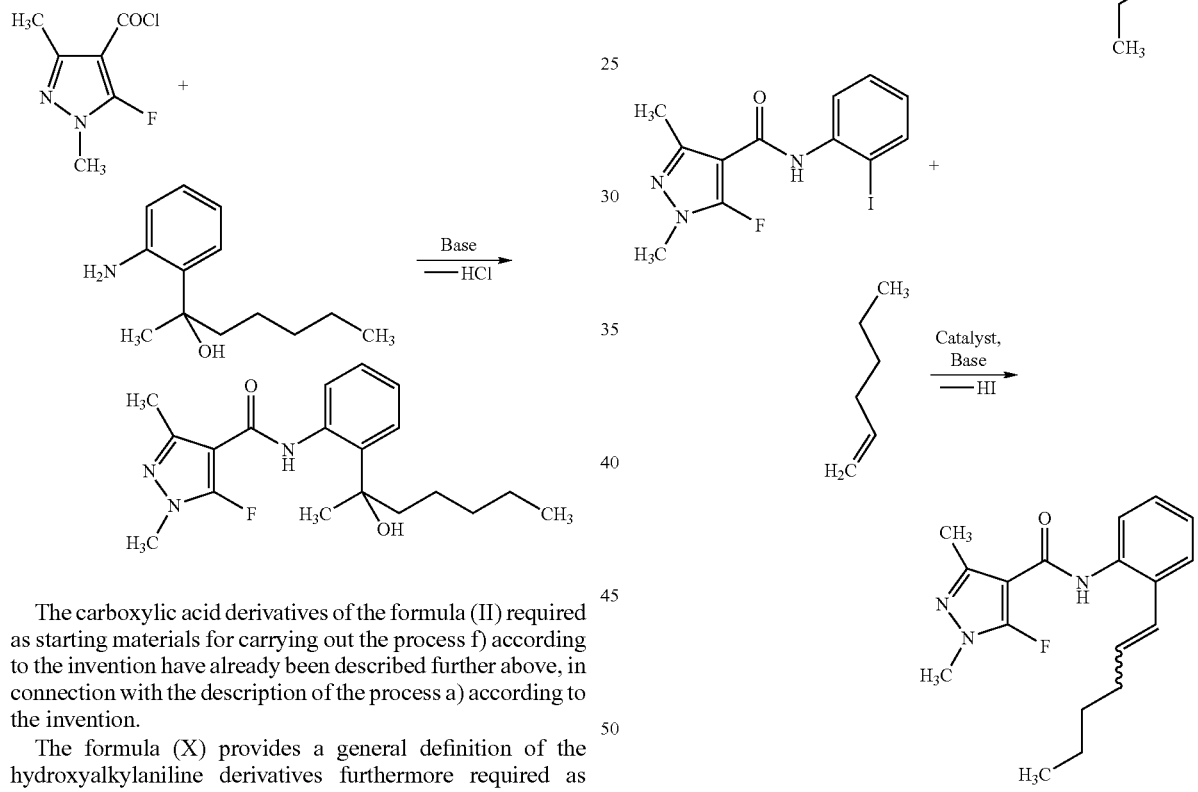

The formula (V) provides a general definition of the halopyrazolylcarboxanilides required as starting materials for carrying out the process d) according to the invention. In this formula (V), R¹, R², G and n preferably and particularly preferably have those meanings which have already been mentioned in connection with the description of the compounds of the formula (I) according to the invention as being preferred and particularly preferred for R¹, R², G and n. Y preferably represents bromine or iodine.

The halopyrazolylcarboxanilides of the formula (V) have hitherto not been known; as novel compounds, they also form part of the subject-matter of the present application.

They are obtained when g) carboxylic acid derivatives of the formula (II)

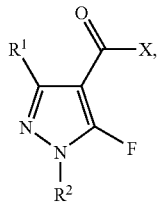

(II)

in which

R$^1$, R$^2$ and X are as defined above, are reacted with a haloaniline of the formula (XI)

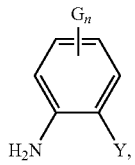

(XI)

in which

G, n and Y are as defined above, if appropriate in the presence of an acid binder and if appropriate in the presence of a diluent.

Using 5-fluoro-1,3-dimethyl-1H-pyrazol-4-carbonyl chloride and 2-iodoaniline as starting materials, the course of the process g) according to the invention can be illustrated by the following formula scheme:

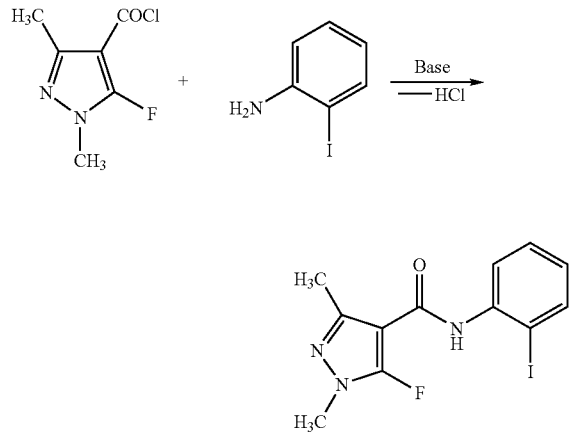

The carboxylic acid derivatives of the formula (II) required as starting materials for carrying out the process g) according to the invention have already been described further above, in connection with the description of the process a) according to the invention.

The formula (XI) provides a general definition of the haloanilines further required as starting materials for carrying out the process g) according to the invention. In this formula (XI), G, n and Y preferably and particularly preferably have those meanings which have already been mentioned in connection with the description of the compounds of the formulae (I) and (V) as being preferred and particularly preferred for G, n and Y.

The haloanilines of the formula (XI) are known chemicals for synthesis.

The formula (VI) provides a general definition of the alkynes furthermore required as starting materials for carrying out the process d) according to the invention.

R$^6$ preferably represents C$_2$-C$_{10}$-alkyl which is optionally mono- to tetrasubstituted by identical or different substituents from the group consisting of fluorine, chlorine, bromine and/or C$_3$-C$_6$-cycloalkyl, where the cycloalkyl moiety for its part may optionally be substituted by halogen and/or C$_1$-C$_4$-alkyl.

R$^6$ particularly preferably represents in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluorocyclopropyl, cyclobutyl, cyclopentyl and/or cyclohexyl.

The alkynes of the formula (VI) are known chemicals for synthesis.

The formula (VII) provides a general definition of the alkenes furthermore alternatively required as starting materials for carrying out the process d) according to the invention.

R$^7$, R$^8$ and R$^9$ independently of one another each preferably represent hydrogen or alkyl which is optionally mono- to tetrasubstituted by identical or different substituents from the group consisting of fluorine, chlorine, bromine and/or C$_3$-C$_6$-cycloalkyl, where the cycloalkyl moiety for its part may optionally be substituted by halogen and/or C$_1$-C$_4$-alkyl and the total number of carbon atoms of the open-chain moiety does not exceed the number 12.

R$^7$, R$^8$ and R$^9$ independently of one another particularly preferably each represent hydrogen or in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluorocyclopropyl, cyclobutyl, cyclopentyl and/or cyclohexyl, where the total number of carbon atoms of the open-chain moiety does not exceed the number 12.

The alkenes of the formula (VII) are known chemicals for synthesis.

Using N-(2-acetylphenyl)-5-fluoro-1,3-dimethyl-1H-pyrazol-4-carboxamide and butyl(triphenyl)-phosphonium iodide as starting materials, the course of process e) according to the invention can be illustrated by the following formula scheme:

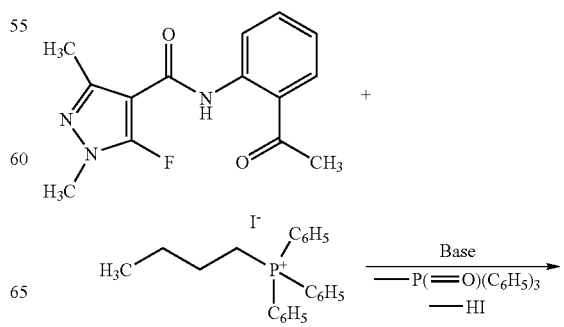

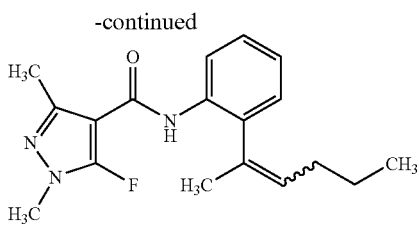

The formula (VIII) provides a general definition of the ketones required as starting materials for carrying out the process e) according to the invention. In this formula (VIII), $R^1$, $R^2$, G and n preferably and particularly preferably have those meanings which have already been mentioned in connection with the description of the compounds of the formula (I) according to the invention as being preferred and particularly preferred for $R^1$, $R^2$, G and n.

$R^{10}$ preferably represents $C_2$-$C_{10}$-alkyl which is optionally mono- to tetrasubstituted by identical or different substituents from the group consisting of fluorine, chlorine, bromine and/or $C_3$-$C_6$-cycloalkyl, where the cycloalkyl moiety for its part may optionally be substituted by halogen and/or $C_1$-$C_4$-alkyl.

$R^{10}$ particularly preferably represents in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluorocyclopropyl, cyclobutyl, cyclopentyl and/or cyclohexyl.

The ketones of the formula (VIII) have hitherto not been known. As novel chemical compounds, they also form part of the subject-matter of the present application.

They are obtained when h) carboxylic acid derivatives of the formula (II)

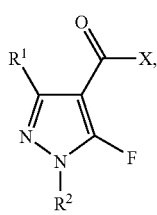

in which $R^1$, $R^2$ and X are as defined above, are reacted with ketoanilines of the formula (XII)

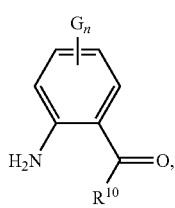

in which $R^{10}$, G and n are as defined above, if appropriate in the presence of an acid binder and if appropriate in the presence of a diluent.

Using 5-fluoro-1,3-dimethyl-1H-pyrazol-4-carbonyl chloride and 1-(2-aminophenyl)ethanone as starting materials, the course of the process h) according to the invention can be illustrated by the following formula scheme:

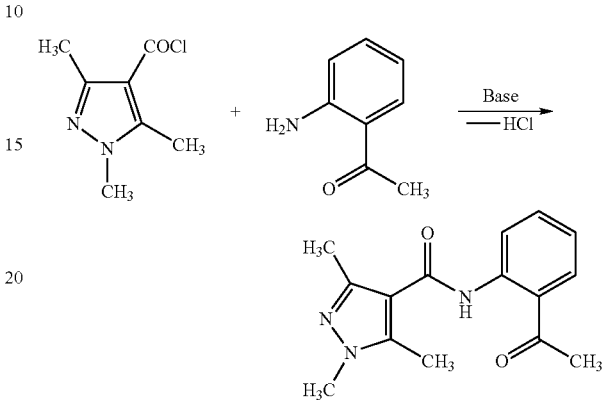

The carboxylic acid derivatives of the formula (II) required as starting materials for carrying out the process h) according to the invention have already been described further above, in connection with the description of the process a) according to the invention.

The formula (XII) provides a general definition of the ketoanilines furthermore required as starting materials for carrying out the process h) according to the invention. In this formula (XII), $R^{10}$, G and n preferably and particularly preferably have those meanings which have already been mentioned in connection with the description of the compounds of the formulae (I) and (VIII) according to the invention as being preferred and particularly preferred for $R^{10}$, G and n.

The ketoanilines of the formula (XII) are generally customary chemicals for synthesis (compare, for example, J. Am. Chem. Soc. 1978, 100(15), 4842-4857 or U.S. Pat. No. 4,032,573).

The formula (IX) provides a general definition of the phosphorus compounds furthermore required as starting materials for carrying out the process e) according to the invention.

$R^{11}$ preferably represents $C_2$-$C_{10}$-alkyl which is optionally mono- to tetrasubstituted by identical or different substituents from the group consisting of chlorine, fluorine, bromine and/or $C_3$-$C_6$-cycloalkyl, where the cycloalkyl moiety for its part may optionally be substituted by halogen and/or $C_1$-$C_4$-alkyl.

$R^{11}$ particularly preferably represents in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluorocyclopropyl, cyclobutyl, cyclopentyl and/or cyclohexyl.

Px preferably represents a grouping $-P^+(C_6H_5)_3$ $Cl^-$, $-P^+(C_6H_5)_3$ $Br^-$, $-P^+(C_6H_5)_3$ $I^-$, $-P(=O)(OCH_3)_3$ or $-P(=O)(OC_2H_5)_3$.

The phosphorus compounds of the formula (IX) are known and/or can be prepared by known processes (compare, for example, Justus Liebigs Ann. Chem. 1953, 580, 44-57 or Pure Appl. Chem. 1964, 9, 307-335).

Suitable diluents for carrying out the processes a), f), g) and h) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloro-methane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol, or amides, such as N,N-dimethylformamide, N,N-dimethylacetamide, N-methyl-formanilide, N-methylpyrrolidone or hexamethylphosphoric triamide.

The processes a), f), g) and h) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcum acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a), f), g) and h) according to the invention, the reaction temperatures can be varied within a relatively wide range. In general, the processes are carried out at temperatures of from 0° C. to 150° C., preferably at temperatures from 0° C. to 80° C.

For carrying out the process a) according to the invention for preparing compounds of the formula (I), in general from 0.2 to 5 mol, preferably from 0.5 to 2 mol, of aniline derivatives of the formula (III) are employed per mole of the carboxylic acid derivative of the formula (II).

For carrying out the process f) according to the invention for preparing compounds of the formula (IV), in general from 0.2 to 5 mol, preferably from 0.5 to 2 mol, of hydroxyalkylaniline derivatives of the formula (X) are employed per mole of the carboxylic acid derivative of the formula (II).

For carrying out the process g) according to the invention for preparing compounds of the formula (V), in general from 0.2 to 5 mol, preferably from 0.5 to 2 mol, of haloaniline of the formula (XI) are employed per mole of the carboxylic acid derivative of the formula (II).

For carrying out the process h) according to the invention for preparing compounds of the formula (VIII), in general from 0.2 to 5 mol, preferably from 0.5 to 2 mol, of ketoaniline of the formula (XII) are employed per mole of the carboxylic acid derivative of the formula (II).

Suitable diluents for carrying out the process b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; ethers, such as diethyl ether, diisopropyl ether, methyl t-butyl ether, methyl t-amyl ether, dioxane, tetrahydrofuran, 1,2-dimethoxyethane, 1,2-diethoxyethane, or anisol, or alcohols, such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether.

The process b) according to the invention is, if appropriate, carried out in the presence of a catalyst. Suitable catalysts are all catalysts which are customarily used for hydrogenations. Examples which may be mentioned are: Raney nickel, palladium or platinum, if appropriate on a support, such as, for example, activated carbon.

Instead of in the presence of hydrogen in combination with a catalyst, the hydrogenation in process b) according to the invention can also be carried out in the presence of triethylsilane.

When carrying out the process b) according to the invention, the reaction temperatures can-be varied within a relatively wide range. In general, the process is carried out at temperatures from 0° C. to 150° C., preferably at temperatures from 0° C. to 80° C.

Suitable diluents for carrying out the process c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethahen; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulfones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process c) according to the invention is, if appropriate, carried out in the presence of an acid. Suitable acids are all inorganic and organic protic acids and also Lewis acids, and also all polymeric acids. These include, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, titanium tetrachloride, tetrabutylorthotitanate, zinc chloride, iron(III) chloride, antimony pentachloride, acidic ion exchangers, acidic alumina and acidic silica gel.

When carrying out the process c) according to the invention, the reaction temperatures can be varied within a relatively wide range. In general, the process is carried out at temperatures of from 0° C. to 150° C., preferably at temperatures of from 0° C. to 80° C.

The processes c) and b) according to the invention can also be carried out in a tandem reaction ("One-pot reaction"). To this end, a compound of the formula (IV) is reacted, if appropriate in the presence of a diluent (suitable diluents as for process c)), and if appropriate in the presence of an acid (suitable acids as for process c)) and in the presence of triethylsilane.

Suitable diluents for carrying out the process d) according to the invention are all inert organic solvents. These preferably include nitriles, such as acetonitrile, propionitrile, n- or i-butyronitrile or benzonitrile, or amides, such as N,N-dimethylformamide, N,N-dimethylacetamide, N-methylformanilide, N-methylpyrrolidone or hexamethylphosphoric triamide.

If appropriate, the process d) according to the invention is carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, calcium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process d) according to the invention is carried out in the presence of one or more catalysts.

Suitable catalysts are in particular palladium salts or complexes. Preferably suitable for this purpose are palladium chloride, palladium acetate, tetrakis(triphenyl-phosphine) palladium or bis(triphenylphosphine)palladium dichloride. It is also possible to generate a palladium complex in the reaction mixture by adding a palladium salt and a complex ligand separately to the reaction.

Suitable ligands are preferably organophosphorus compounds. Examples which may be mentioned are: triphenylphosphine, tri-o-tolylphosphine, 2,2'-bis(diphenyl-phosphino)-1,1'-binaphthyl, dicyclohexylphosphinebiphenyl, 1,4-bis(diphenyl-phosphino)butane, bisdiphenylphosphinoferrocene, di(tert-butylphosphino)biphenyl, di(cyclohexylphosphino)biphenyl, 2-dicyclohexylphosphino-2'-N,N-dimethylamino-biphenyl, tricyclohexylphosphine, tri-tert-butylphosphine. However, it is also possible to dispense with ligands.

The process d) according to the invention is furthermore, if appropriate, carried out in the presence of a further metal salt, such as copper salts, for example copper(I) iodide.

When carrying out the process d) according to the invention, the reaction temperatures can be varied within a relatively wide range. In general, the process is carried out at temperatures of from 20° C. to 180° C., preferably at temperatures of from 50° C. to 150° C.

For carrying out the process d) according to the invention for preparing compounds of the formula (I), in general from 1 to 5 mol, preferably from 1 to 2 mol, of alkyne of the formula (VI) or alkene of the formula (VII) are employed per mole of the halopyrazolylcarboxanilide of the formula (V).

Suitable diluents for carrying out the process e) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether.

The process e) according to the invention is, if appropriate, carried out in the presence of a suitable acid acceptor. Suitable acid acceptors are all customary strong bases. These preferably include alkaline earth metal or alkali metal hydrides, hydroxides, amides, alkoxides or alkali metal hydrocarbon compounds, such as, for example, sodium hydride, sodium hydroxide, potassium hydroxide, sodium amide, lithium diisopropylamide, sodium methoxide, sodium ethoxide, potassium tert-butoxide, methyl lithium, phenyl lithium or butyl lithium.

When carrying out the process e) according to the invention, the reaction temperatures can be varied within a relatively wide range. In general, the process is carried out at temperatures of from −80° C. to 150° C., preferably at temperatures of from −30° C. to 80° C.

For carrying out the process e) according to the invention for preparing compounds of the formula (I), in general from 1 to 5 mol, preferably from 1 to 2 mol, of phosphorus compound of the formula (IX) are employed per mole of the ketone of the formula (VIII).

All processes according to the invention are generally carried out under atmospheric pressure. However, it is also possible to operate under elevated or reduced pressure—in general between 0.1 bar and 10 bar.

The substances according to the invention have potent microbicidal activity and can be employed for controlling undesirable microorganisms, such as fungi and bacteria, in crop protection and in the protection of material.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fingal and bacterial diseases which come under the generic names listed above may be mentioned as examples, but not by way of limitation:

Xanthomonas species, such as, for example, *Xanthomonas campestris* pv. *oryzae*;

Pseudomonas species, such as, for example, *Pseudomonas syringae* pv. *lachrymans*;

Erwinia species, such as, for example, *Erwinia amylovora*;

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Bremia species, such as, for example, *Bremia lactucae*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Sclerotinia species, such as, for example, *Sclerotinia sclerotiorum*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae*; and

Pseudocercosporella species, such as, for example, *Pseudocercosporella herpotrichoides*.

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling cereal diseases, such as, for example, against Pyrenophora species, and diseases in viticulture, and in fruit and vegetable growing, such as, for example, against Altemaria or Podosphaera species.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. They can also be used as intermediates and precursors for the synthesis of further active compounds.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids particularly preferably wood.

Microorganisms capable of degrading or changing the industrial materials which may be mentioned are, for example, bacteria, fingi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*, and
Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fuingicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, carpropamide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenhexamide, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine, hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, iprovalicarb, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur,
quinconazole, quintozene (PCNB), quinoxyfen,
sulphur and sulphur preparations, spiroxamines,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole,
uniconazole,
validamycin A, vinclozolin, viniconazole,
zarilamide, zineb, ziram and also
Dagger G, OK-8705, OK-8801,
α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[(3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metarhizium flavoviride,* methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen,
quinalphos, ribavirin,
salithion, sebufos, silafluofen, spinosad, spirodiclofen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI 5302, Zeta-cypermethrin, Zolaprofos
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N''-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)-4-[3-(5-trifluoromethylpyridine-2-yloxy)-propoxy]-benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fingi, (for example against Candida species, such as *Candida albicans, Candida glabrata*), and *Epidermophyton floccosum,* Aspergillus species, such as *Aspergillus niger* and *Aspergillus fumigatus,* Trichophyton species, such as *Trichophyton mentagrophytes,* Microsporon species such as *Microsporon canis* and *audouinii.* The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts with active compounds according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better. quality and/or a higher nutritional value of the harvested products, better storage stability and/or processability of the harvested products. Further and particularly emphasized examples of such properties are a better defence of the plants against animal and microbial pests, such as against insects, mites, phytopathogenic fingi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasised are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasised are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STSO (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) according to the invention. The preferred ranges stated above for the active compounds also apply to the treatment of these plants. Particular emphasis is given to the treatment of plants with the compounds specifically mentioned in the present text.

PREPARATION EXAMPLES

Example 1

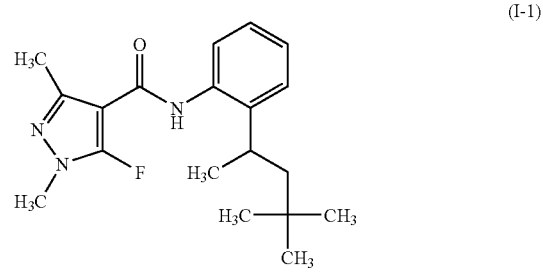

(I-1)

Process (a):

A mixture of 382.6 mg (2 mmol) of 2-(1,3,3-trimethylbutyl)aniline, 353.2 mg (2 mmol) of 5-fluoro-1,3-dimethyl-1H-pyrazol-4-carbonyl chloride and 276.4 mg (2 mmol) of potassium carbonate in 25 ml of acetonitrile is stirred at room temperature overnight. 30 ml of saturated ammonium chloride solution are added, and the mixture is extracted with 30 ml of ethyl acetate. The combined organic phases are dried over magnesium sulphate and concentrated under reduced pressure. The residue is chromatographed on silica gel using cyclohexane/ethyl acetate (starting with pure cyclohexane and finally with 80% ethyl acetate).

This gives 280 mg (42% of theory) of 5-fluoro-1,3-dimethyl-N-[2-(1,3,3-trimethylbutyl)phenyl]-1H-pyrazol-4-carboxamide of melting point 78-80° C.

Example 2

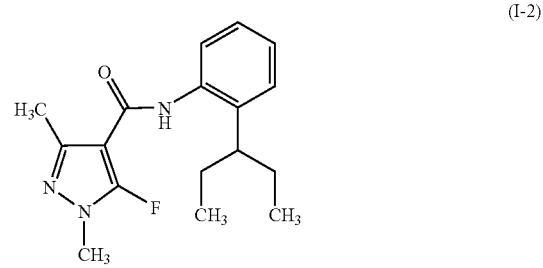

(I-2)

Process (b)

In the presence of 500 mg of 5% Pd/C, 540 mg (1.792 mmol) of N-[2-(1-ethenylpropyl)phenyl]-5-fluoro-1,3-dimethyl-1H-pyrazol-4-carboxamide (I-24) in 50 ml of methanol are hydrogenated under a hydrogen pressure of 100 bar at 80° C. for 5 hours. The catalyst is filtered off, the filter residue is washed with 2×50 ml of methanol and the motherliquor is concentrated under reduced pressure. The residue is chromatographed on silica gel using cyclohexane/ethyl acetate 4:1.

This gives 150 mg (30% of theory) of N-[2-(1-ethylpropyl)phenyl]-5-fluoro-1,3-dimethyl-1H-pyrazol-4-carboxamide as pale yellow crystals.

HPLC: logP=3.01.

Example 3

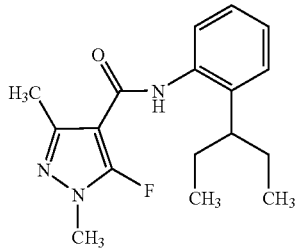

(I-2)

Processes (c) and (b) as Tandem Reaction

At room temperature, 450 mg (1.41 mmol) of N-[2-(1-ethyl-1-hydroxypropyl)-phenyl]-5-fluoro-1,3-dimethyl-1H-pyrazol-4-carboxamide (IV-1) in 10 ml of dichloromethane are, after addition of 1.6 g (14.1 mmol) of trifluoroacetic acid and 0.16 g (1.41 mmol) of triethylsilane, stirred for 1 hour. The reaction solution is adjusted to pH 7 using saturated sodium bicarbonate solution and the organic phase is separated off, dried over magnesium sulphate and concentrated under reduced pressure. The residue is chromatographed on silica gel using cyclohexane/ethyl acetate 4:1.

This gives 120 mg (20% of theory) of N-[2-(1-ethylpropyl)phenyl]-5-fluoro-1,3-dimethyl-1H-pyrazol-4-carboxamide as pale yellow crystals.

HPLC: logp=3.01.

Example 4

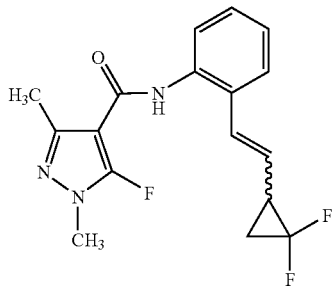

(I-3)

Process (d)

0.718 g (2 mmol) of the iodoanilide 5-fluoro-N-(2-iodophenyl)-1,3-dimethyl-1H-pyrazol-4-carboxamide, 0.25 g (2.5 mmol) of 1,1-difluoro-2-vinylcyclopropane and 0.33 ml (2.4 mmol) of triethylamine are dissolved in 4 ml of dimethylformamide, and argon is then passed through the reaction solution for 5 minutes. 20 mg (0.09 mmol) of palladium acetate are then added, and the mixture is stirred at 100° C. in a closed airtight vessel for 16 hours. After the reaction has ended, the mixture is applied to a silica cartridge and eluted with ethyl acetate. The eluate is admixed with activated carbon, filtered and concentrated under reduced pressure. The residue is chromatographed on silica gel using cyclohexane/ethyl acetate (3:1 to 1:1).

This gives 154 mg (23% of theory) of N-{2-[2-(2,2-difluorocyclopropyl)ethenyl]-phenyl}-5-fluoro-1,3-dimethyl-1H-pyrazol-4-carboxamide.

HPLC: logP=2.59.

Example 5

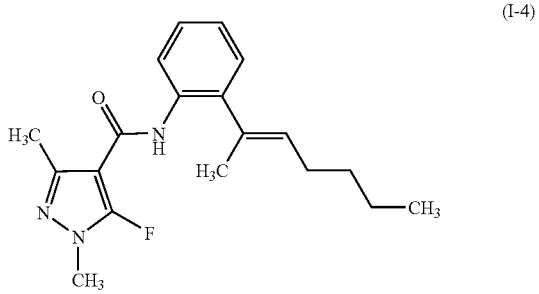

(I-4)

Process (e):

227 mg (0.55 mmol) of n-butyltriphenylphosphonium bromide are suspended in 2 ml of tetrahydrofuran and, at −30° C., 0.34 ml (0.55 mmol) of an n-BuLi solution in hexane are added and the mixture is stirred at this temperature for 20 min. A suspension of 138 mg (0.5 mmol) of N-(2-acetylphenyl)-5-fluoro-1,3-dimethyl-1H-pyrazol-4-carboxamide in 2 ml of tetrahydrofuran is then added, and the mixture is stirred without fuirther cooling for 16 hours. 3 ml of water are added, and the mixture is extracted 3 times with in each case 20 ml of ethyl acetate. The combined organic phases are dried over magnesium sulphate and concentrated under reduced pressure. The residue is chromatographed on silica gel using cyclohexane/ethyl acetate (5:1 to 1:1).

This gives 17 mg (10% of theory) of 5-fluoro-1,3-dimethyl-N-[2-(1-methyl-1-hexenyl)phenyl]-1H-pyrazol-4-carboxamide.

HPLC: logP=4.36.

The compounds of the formula (I) listed in Table 1 below are obtained analogously to Examples 1 to 5 and in accordance with the statements in the general descriptions of the processes.

| Ex. No. | Compound | logP | m.p. (°C.) |
|---|---|---|---|
| I-5 | | | |
| I-6 | | | 114 |
| I-7 | | | 92-94 |
| I-8 | | | |
| I-9 | | 4.36 | 132-134 |
| I-10 | | 3.37 | 109-111 |
| I-11 | | | |
| I-12 | | | 97 |
| I-13 | | | 143 |
| I-14 | | | 151 |

-continued
| Ex. No. | Compound | logP | m.p. (° C.) |
|---|---|---|---|
| I-15 | 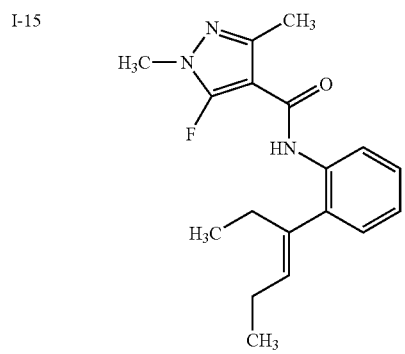 | | |
| I-16 | 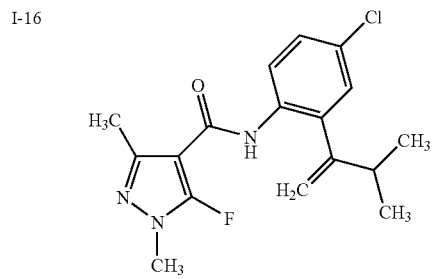 | 4.11 | 155-157 |
| I-17 | 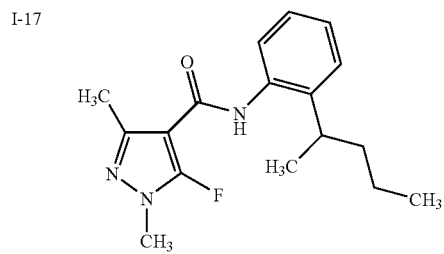 | 3.01 | 84-87 |
| I-18 | 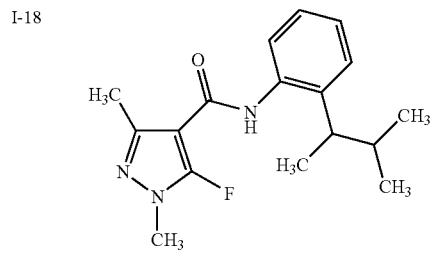 | 2.92 | 85 |
| I-19 | 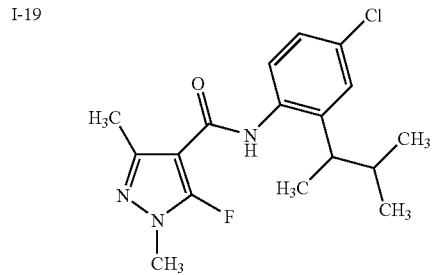 | 3.43 | 123-124 |
-continued
| Ex. No. | Compound | logP | m.p. (° C.) |
|---|---|---|---|
| I-20 | 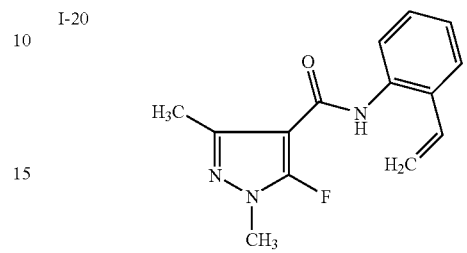 | 1.92 | |
| I-21 | 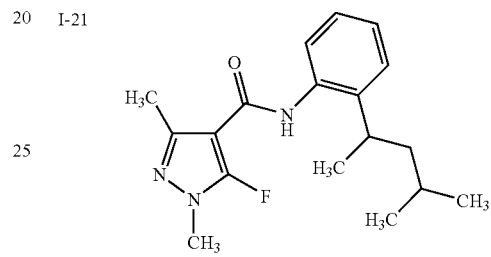 | 3.26 | |
| I-22 | 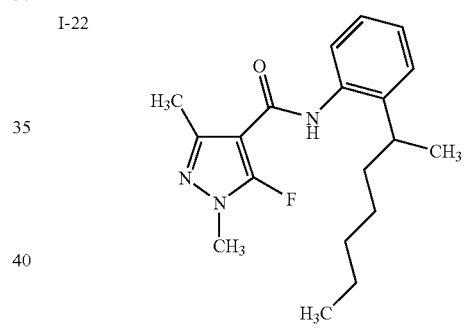 | 3.83 | |
| I-23 | 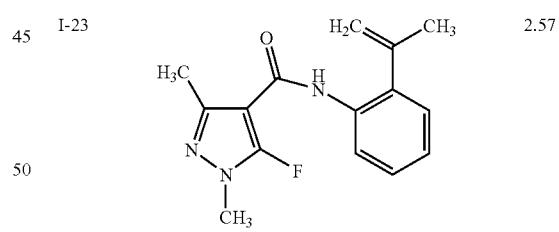 | 2.57 | |
| I-24 | 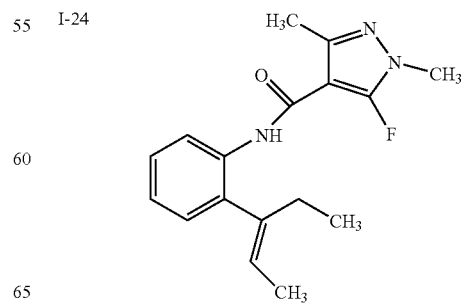 | 3.45 | |

-continued
| Ex. No. | Compound | logP | m.p. (° C.) |
|---|---|---|---|
| I-25 | 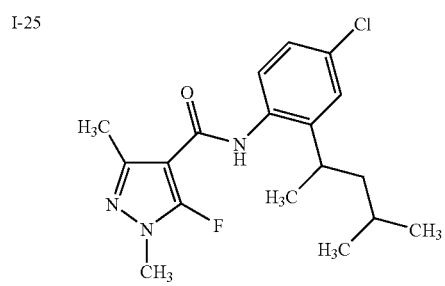 | 3.82 | 111-13 |
| I-26 | 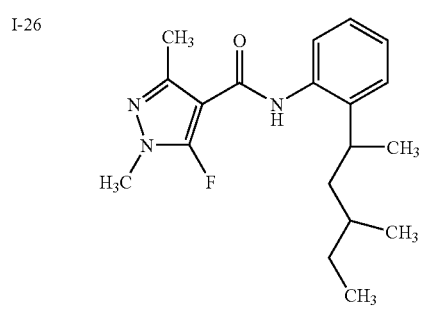 | 3.67 | |
| I-27 | 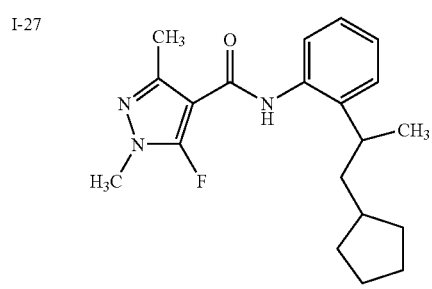 | 3.82 | |
| I-28 | 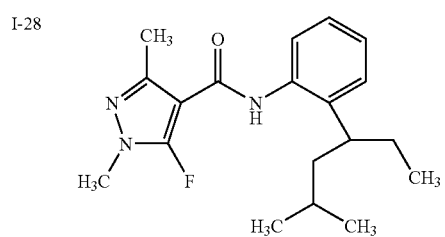 | 3.73 | |
| I-29 | 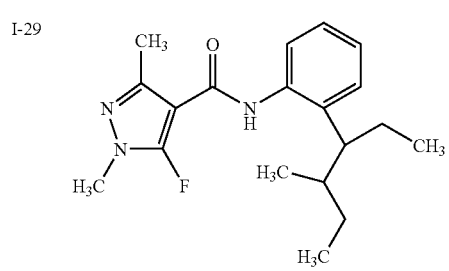 | 3.74 | |
-continued
| Ex. No. | Compound | logP | m.p. (° C.) |
|---|---|---|---|
| I-30 | 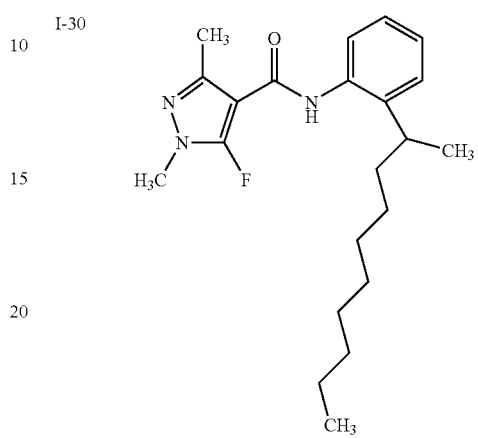 | 5.29 | |
| I-31 | 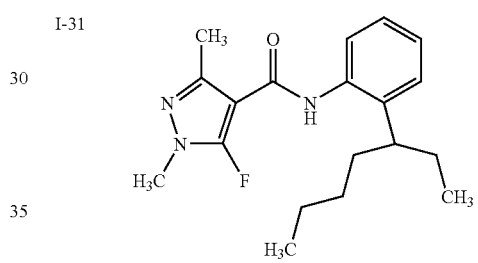 | 3.85 | |
| I-32 | 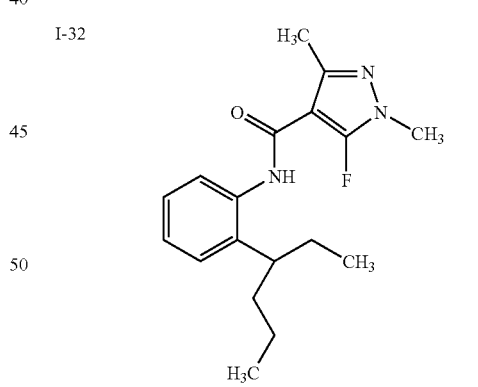 | 3.42 | |
| I-33 | 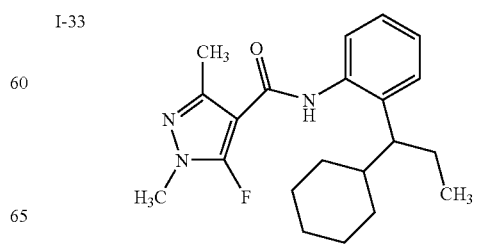 | 4.34 | |

-continued

| Ex. No. | Compound | logP | m.p. (°C.) |
|---|---|---|---|
| I-34 | | 4.22 | |
| I-35 | | 4.11 | |
| I-36 | | 3.76 | |
| I-37 | | 4.49 | |
| I-38 | | 3.37 | |
| I-39 | | 4.24 | |
| I-40 | | 3.28 | |
| I-41 | | 3.32 | |
| I-42 | | 3.82 | |
| I-43 | | 3.05 | |

-continued

| Ex. No. | Compound | logP | m.p. (°C.) |
|---|---|---|---|
| I-44 | | 3.16 | |
| I-45 | | 4.2 | |
| I-46 | | 3.09 | |
| I-47 | | 4.01 | |
| I-48 | | 3.44 | |
| I-49 | | 3.47 | |

-continued

| Ex. No. | Compound | logP | m.p. (°C.) |
|---|---|---|---|
| I-50 | | 2.86 | |
| I-51 | | | |
| I-52 | | 5.08 | |
| I-53 | | 3.59 | |
| I-54 | | 4.90 | |

Preparation of the Intermediates

Example (IV-1)

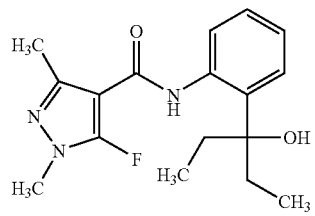

Process (f):

At room temperature, 358.5 mg (2 mmol) of 3-(2-aminophenyl)-3-pentanol and 353.2 mg (2 mmol) of 5-fluoro-1,3-dimethyl-1H-pyrazol-4-carbonyl chloride are stirred with 276.4 mg (2 mmol) of potassium carbonate in 15 ml of acetonitrile for 16 hours. 30 ml of saturated ammonium chloride solution are added, and the mixture is then extracted with 30 ml of ethyl acetate. The combined organic phases are washed with 30 ml of concentrated sodium chloride solution, dried over magnesium sulphate and concentrated under reduced pressure. The residue is chromatographed on silica gel using cyclohexane/ethyl acetate (starting with pure cyclohexane and finally with 80% ethyl acetate).

This gives 350 mg (45% of theory) of N-[2-(1-ethyl-1-hydroxypropyl)phenyl]-5-fluoro-1,3-dimethyl-1H-pyrazol-4-carboxamide as colourless crystals.

HPLC: logP=2.47.

The compounds of the formula (IV) listed in Table 2 below are obtained analogously to Example (IV-1) and in accordance with the statements in the general descriptions of the process.

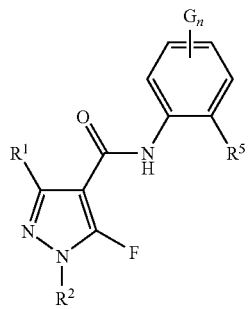

(IV)

| Ex. No. | Compound | logP | m.p. (° C.) |
|---|---|---|---|
| IV-2 | 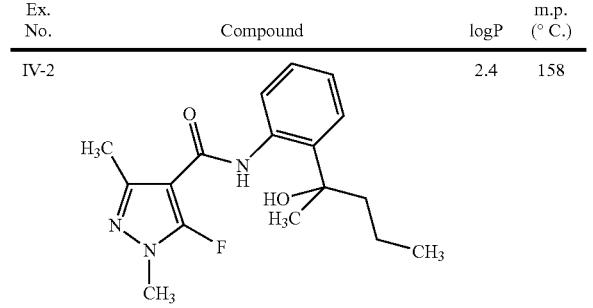 | 2.4 | 158 |
| IV-3 | 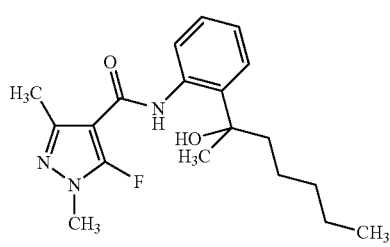 | 3.13 | |
| IV-4 | 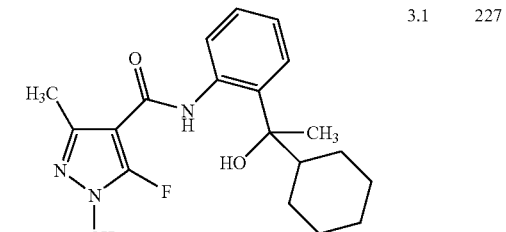 | 3.1 | 227 |
| IV-5 | 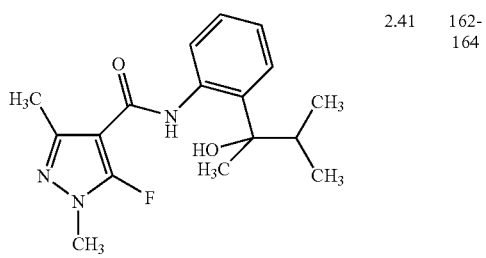 | 2.41 | 162-164 |
| IV-6 | 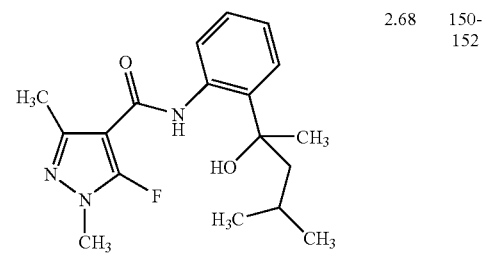 | 2.68 | 150-152 |

-continued (IV)

| Ex. No. | Compound | logP | m.p. (° C.) |
|---|---|---|---|
| IV-7 | | | 173 |
| IV-8 | | | 161 |
| IV-9 | | | 165 |
| IV-10 | | | 181 |

-continued (IV)

| Ex. No. | Compound | logP | m.p. (° C.) |
|---|---|---|---|
| IV-11 | | | 167 |
| IV-12 | | 2.99 | |
| IV-13 | | 3.11 | |

Example (V-1)

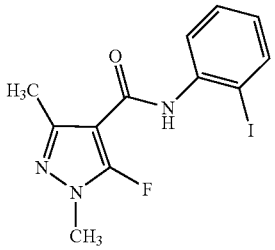

Process (g):

A mixture of 5.86 g (42 mmol) of potassium carbonate and 6.2 g (28.3 mmol) of 2-iodoaniline in 100 ml of acetonitrile is stirred at room temperature for 10 min. A solution of 5 g (28.3 mmol) of 5-fluoro-1,3-dimethyl-1H-pyrazol-4-carbonyl chloride in 10 ml of acetonitrile is added slowly, and the mixture is stirred under reflux for 16 hours. The reaction mixture is concentrated under reduced pressure, and 200 ml of ethyl acetate and 100 ml of water are added. The organic phase is separated off and the aqueous phase is extracted 3 times with 200 ml of ethyl acetate. The combined organic phases are dried over magnesium sulphate and concentrated under reduced pressure. The residue is stirred in 50 ml of ether.

This gives 4.78 g (47% of theory) of 5-fluoro-N-(2-iodophenyl)-1,3-dimethyl-1H-pyrazol-4-carboxamide.

HPLC: logP=2.44.

Example (VIII-1)

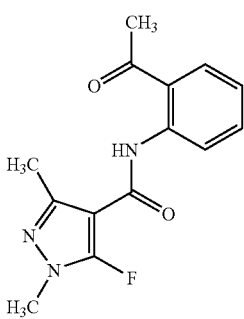

Process (h):

A solution of 8 g (45 mmol) of 5-fluoro-1,3-dimethyl-1H-pyrazol-4-carbonyl chloride in 30 ml of acetonitrile is added to a mixture of 10.4 g (76 mmol) of potassium carbonate and 5.1 g (38 inmol) of 2-aminoacetophenone in 40 ml of acetonitrile, and the mixtured is stirred at 80° C. for 16 hours. The reaction mixture is concentrated under reduced pressure, and 200 ml of ethyl acetate and 70 ml of water are added. The organic phase is separated off and the aqueous phase is extracted 3 times with 200 ml of ethyl acetate. The combined organic phases are dried over magnesium sulphate and concentrated under reduced pressure. The residue is filtered through a silica gel cartridge using dichloromethane, the filtrate is concentrated under reduced pressure and the crude product is saturated with diisopropyl ether.

This gives 2.5 g (24% of theory) of N-(2-acetylphenyl)-5-fluoro-1,3-dimethyl-1H-pyrazol-4-carboxamide.

HPLC: logP=2.15.

The logP values given in the preparation examples and tables above are determined in accordance with EEC Directive 79/831 Annex V.A8 by HPLC (High Performance Liquid Chromatography) using a reversed-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

The calibration is carried out using unbranched alkan-2-ones (having 3 to 16 carbon atoms), with known logP values (determination of the logp values by the retention times using linear interpolation between two successive alkanones).

The lambda max values were determined in the maxima of the chromatographic signals using the UV spectra from 200 nm to 400 nm.

USE EXAMPLES

Example A

| | *Pyrenophora teres* test (barley)/protective |
|---|---|
| Solvent: | 25 parts by weight of N,N-dimethylacetamide |
| Emulsifier: | 0.6 parts by weight of alkylaryl polyglycol ether |

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at a temperature of about 20° C. and a relative atmospheric humidity of about 80%.

Evaluation is carried out 7 days after the inoculation. 0% means an efficacy which corresponds to that of the control, whereas an efficacy of 100% means that no infection is observed.

In this test, for example, compounds of the Preparation Examples exhibit, at an application rate of 250 g/ha, an efficacy of 95% or more.

TABLE A

Pyrenophora teres test (barley)/protective

| Active compound according to the invention | Application rate of active compound in g/ha | Efficacy in % |
|---|---|---|
| 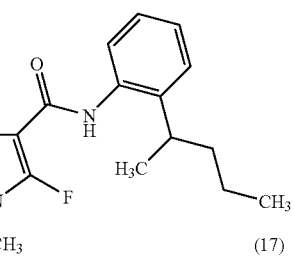 (17) | 250 | 100 |
| (18) | 250 | 100 |

Example B

Podosphaera test (apple)/protective

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

In this test, for example, compounds of the Preparation Examples exhibit, at an application rate of 100 g/ha, an efficacy of 90% or more.

TABLE B

Podosphaera test (apple)/protective

| Active compound according to the invention | Application rate of active compound in g/ha | Efficacy in % |
|---|---|---|
| 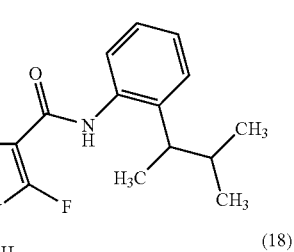 (10) | 100 | 90 |
| (17) | 100 | 100 |
| (18) | 100 | 100 |
| (19) | 100 | 100 |

Example C

| *Alternaria* test (tomato)/protective | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of Alternaria solani and then remain at 100% rel. humidity and 20° C. for 24 h. The plants then remain at 96% rel. atmospheric humidity and a temperature of 20° C.

Evaluation was carried out 7 days after the inoculation. 0% means an efficacy which corresponds to that of the control, whereas an efficacy of 100% means that no infection is observed.

In this test, for example, compounds of the Preparation Examples exhibit, at an application rate of 750 g/ha, an efficacy of 90% or more.

TABLE C

*Alternaria* test (tomato)/protective

| Active compound | Application rate of active compound in g/ha | Efficacy in % |
|---|---|---|
| (17) | 750 | 95 |
| (18) | 750 | 95 |
| (21) | 750 | 100 |

What is claimed is:

1. A pyrazolylcarboxanilide of formula (I)

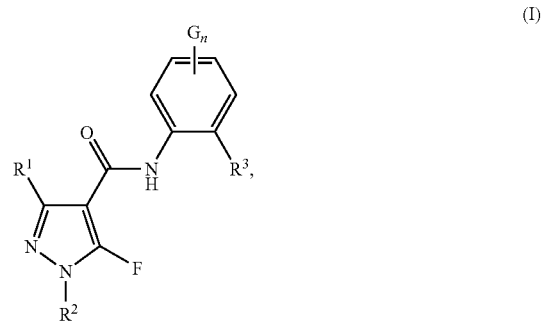

in which
R$^1$ represents hydrogen, cyano, halogen, nitro, $C_1$-$C_4$-alkyl, $C_1$-$C_4$-haloalkyl having 1 to 5 halogen atoms, $C_3$-$C_6$-cycloalkyl, $C_1$-$C_4$-alkoxy, $C_1$-$C_4$-haloalkoxy having 1 to 5 halogen atoms, $C_1$-$C_4$-alkylthio, $C_1$-$C_4$-haloalkylthio having 1 to 5 halogen atoms, or aminocarbonyl-$C_1$-$C_4$-alkyl, R$^2$ represents hydrogen, $C_1$-$C_4$-alkyl, $C_1$-$C_6$-haloalkyl having 1 to 5 halogen atoms, $C_2$-$C_6$-alkenyl, $C_3$-$C_6$-cycloalkyl, $C_1$-$C_4$-alkylthio-$C_1$-$C_4$-alkyl, $C_1$-$C_4$-haloalkylthio-$C_1$-$C_4$-alkyl having 1 to 5 halogen atoms, $C_1$-$C_4$-alkoxy-$C_1$-$C_4$-alkyl, or $C_1$-$C_4$-haloalkoxy-$C_1$-$C_4$-alkyl having 1 to 5 halogen atoms, G represents halogen, $C_1$-$C_4$-alkyl, or $C_5$-$C_6$-alkyl, R$^3$ represents unsubstituted $C_5$-$C_{12}$-alkyl; represents $C_1$-$C_{20}$-alkyl that is mono- or polysubstituted by identical or different substituents selected from the group consisting of halogen and $C_3$-$C_6$-cycloalkyl; or represents $C_2$-$C_{20}$-alkenyl or $C_2$-$C_{20}$-alkynyl, each of which is optionally mono- or polysubstituted by identical or different substituents selected from the group consisting of halogen and $C_3$-$C_6$-cycloalkyl, where the cycloalkyl moiety is optionally mono- or polysubstituted by identical or different substituents selected from the group consisting of halogen and $C_1$-$C_4$-alkyl, and n represents 0, 1, or 2.

2. A pyrazolylcarboxanilide according to claim 1 in which G represents halogen or $C_1$-$C_4$-alkyl, and R$^1$, R$^2$, R$^3$, and n are as defined in claim 1.

3. A pyrazolylcarboxanilide according to claim 1 in which
R$^1$ represents hydrogen, cyano, halogen, nitro, $C_1$-$C_4$-alkyl, $C_1$-$C_4$-haloalkyl having 1 to 5 fluorine, chlorine, and/or bromine atoms, $C_3$-$C_6$-cycloalkyl, $C_1$-$C_4$-alkoxy, $C_1$-$C_4$-haloalkoxy having 1 to 5 fluorine, chlorine, and/or bromine atoms, $C_1$-$C_4$-alkylthio, $C_1$-$C_4$-haloalkylthio having 1 to 5 fluorine, chlorine, and/or bromine atoms, or aminocarbonyl-$C_1$-$C_4$-alkyl, R$^2$ represents hydrogen, $C_1$-$C_4$-alkyl, $C_1$-$C_6$-haloalkyl having 1 to 5 fluorine, chlorine, and/or bromine atoms, $C_2$-$C_6$-alkenyl, $C_3$-$C_6$ cycloalkyl, $C_1$-$C_4$-alkylthio-$C_1$-$C_4$-alkyl, $C_1$-$C_4$-haloalkylthio-$C_1$-$C_4$-alkyl having 1 to 5 fluorine, chlorine, and/or bromine atoms, $C_1$-$C_4$-alkoxy-$C_1$-$C_4$-alkyl, or $C_1$-$C_4$-haloalkoxy-$C_1$-$C_4$-alkyl having 1 to 5 fluorine, chlorine, and/or bromine atoms, G represents halogen, $C_1$-$C_4$-alkyl, or $C_5$-$C_6$-alkyl, R$^3$ represents unsubstituted $C_5$-$C_{12}$-alkyl; represents $C_2$-$C_{12}$-alkyl that is mono- to tetrasubstituted by identical or different substituents selected from the group consisting of fluorine, chlorine, bromine, and $C_3$-$C_6$- cycloalkyl; or represents $C_2$-$C_{12}$-alkenyl or $C_2$-$C_{12}$-alkynyl, each of which is optionally mono- to tetrasubstituted by identical or different substituents selected from the group consisting of fluorine, chlorine, bromine, and $C_3$-$C_6$-cycloalkyl, where the cycloalkyl moiety is optionally mono- to tetrasubstituted by identical or different substituents selected from the group consisting of halogen and $C_1$-$C_4$-alkyl, and n represents 0, 1, or 2.

4. A pyrazolylcarboxanilide according to claim 3 in which G represents halogen or $C_1$-$C_4$-alkyl, and
$R^1$, $R^2$, $R^3$, and n are as defined in claim 3.

5. A pyrazolylcarboxanilide according to claim 1 in which
$R^1$ represents hydrogen, methyl, ethyl, n- or i-propyl, n-, i-, s-, or t-butyl, trifluoromethyl, or trifluoroethyl,
$R^2$ represents hydrogen, methyl, ethyl, n- or i-propyl, n-, i-, s-, or t-butyl, trifluoromethyl, or trifluoroethyl,
G represents fluorine, chlorine, methyl, ethyl, t-butyl, or 2,4-dimethylbutyl,
$R^3$ represents straight-chain or branched pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl, or decynyl, each of which may be attached at any position and each of which is optionally mono- to tetrasubstituted by identical or different substituents selected from the group consisting of fluorine, cyclo-propyl, difluorocyclopropyl, cyclobutyl, cyclopentyl, and cyclohexyl, and
n represents 0, 1 or 2.

6. A pyrazolylcarboxanilide according to claim 5 in which G represents fluorine, chlorine, or methyl, and
$R^1$, $R^2$, $R^3$, and n are as defined in claim 5.

7. A pyrazolylcarboxanilide according to claim 1 in which
$R^1$ represents methyl, and
$R^2$ represents methyl.

8. A pyrazolylcarboxanilide according to claim 1 in which $R^3$ represents unsubstituted $C_5$-$C_6$-alkyl.

9. A pyrazolylcarboxanilide according to claim 1 in which n represents 0.

10. A pyrazolylcarboxanilide according to claim 1 in which
$R^1$ represents methyl,
$R^2$ represents methyl,
$R^3$ represents unsubstituted $C_5$-$C_{12}$-alkyl, and
n represents 0.

11. A pyrazolylcarboxanilide according to claim 10 in which
$R^3$ represents unsubstituted $C_5$-$C_6$-alkyl.

12. A pyrazolylcarboxanhlide according to claim 10 in which
$R^3$ represents 1,3-dimethylbutyl.

13. A process for preparing a compound of formula (I) according to claim 1 comprising
(a) reacting a carboxylic acid derivative of formula (II)

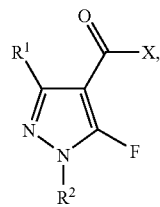

(II)

in which
$R^1$ and $R^2$ are as defined for formula (I) in claim 1, and
X represents halogen,
with an aniline derivative of formula (III)

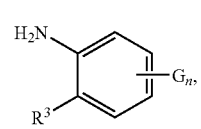

(III)

in which G, $R^3$, and n are as defined for formula (I) in claim 1, optionally in the presence of an acid binder and optionally in the presence of a diluent, or (b) hydrogenating a pyrazolylcarboxanilide of formula (Ia)

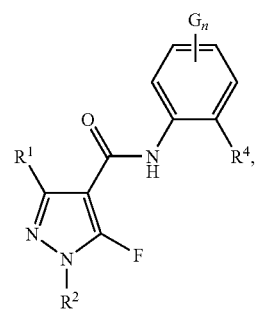

(Ia)

in which
$R^1$, $R^2$, G, and n are as defined for formula (I) in claim 1, and
$R^4$ represents $C_2$-$C_{20}$-alkenyl or $C_2$-$C_{20}$-alkynyl, each of which is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl,
optionally in the presence of a diluent and optionally in the presence of a catalyst, or (c) dehydrating a hydroxyalkylpyrazolylcarboxanilide of formula (IV)

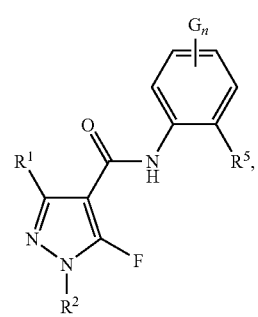

(IV)

in which
$R^1$, $R^2$, G and n are as defined for formula (I) in claim 1, and
$R^5$ represents $C_5$-$C_{12}$-hydroxyalkyl that is optionally additionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl,
optionally in the presence of a diluent and optionally in the presence of an acid, or
(d) reacting a halopyrazolylcarboxanilide of formula (V)

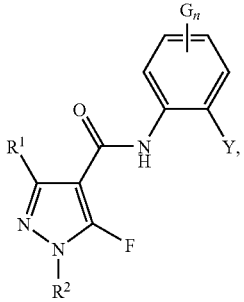
(V)

in which
$R^1$, $R^2$, G, and n are as defined for formula (I) in claim 1, and
Y represents bromine or iodine,
with an alkyne of formula (VI)

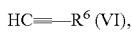
HC≡—$R^6$ (VI), in which $R^6$ represents $C_2$-$C_{18}$-alkyl that is optionally mono- or polysubstituted by identical or different substituents selected from the roup consisting of halogen and $C_3$-$C_6$-cycloalkyl, where the cycloalkyl moiety is optionally substituted by halogen and/or $C_1$-$C_4$-alkyl, or
with an alkene of formula (VII)

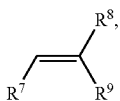
(VII)

in which $R^7$, $R^8$, and $R^9$ independently of one another each represent hydrogen or alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl and where the total number of carbon atoms of the open-chain moiety does not exceed the number 20,
optionally in the presence of a diluent, optionally in the presence of an acid binder, and in the presence of one or more catalysts, or (e) reacting a ketone of formula (VIII)

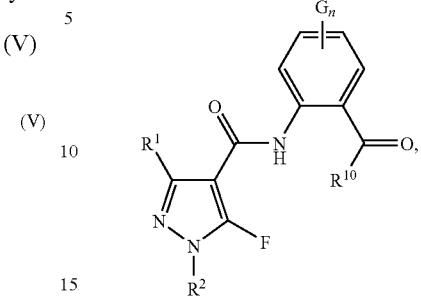
(VIII)

in which
$R^1$, $R^2$, G, and n are as defined for formula (I) in claim 1,
$R^{10}$ represents hydrogen or $C_1$-$C_{18}$-alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl,
with a phosphorus compound of formula (IX)

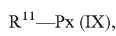
$R^{11}$—Px (IX), in which
$R^{11}$ represents hydrogen or $C_1$-$C_{18}$-alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl, and
Px represents a group —$P^+(C_6H_5)_3Cl^-$, —$P^+(C_6H_5)_3Br^-$, —$P^+(C_6H_5)_3 I^-$, —$P(=O)(OCH_3)_3$, or —$P(=O)(OC_2H_5)_3$,
with the proviso that when $R^{10}$ and $R^{11}$ are both unsubstituted alkyl, the total number of alkyl carbon atoms in $R^{10}$ and $R^{11}$ together is from 5 to 12, optionally in the presence of a diluent.

14. A composition for controlling phytopathogenic fungi, bacteria, and viruses comprising one or more pyrazolylcarboxanilides of formula (I) according to claim 1 and one or more extenders and/or surfactants.

15. A method for controlling phytopathogenic fungi, bacteria, and viruses comprising applying an effective amount of a pyrazolylcarboxanilide of formula (I) according to claim 1 to a microorganism and/or its habitat.

16. A process for preparing a composition for controlling phytopathogenic fungi, bacteria, and viruses comprising mixing a pyrazolylcarboxanilide of formula (I) according to claim 1 with one or more extenders and/or surfactants.

\* \* \* \* \*